United States Patent
Butner

(10) Patent No.: US 11,394,107 B2
(45) Date of Patent: Jul. 19, 2022

(54) TELEPHONE HANDSET PROVIDED WITH A REMEDIAL SIGNAL GENERATOR

(71) Applicant: TRUST TECHNOLOGY WORLD DMCC, Dubai (AE)

(72) Inventor: Wayne Butner, Vancouver (CA)

(73) Assignee: TRUST TECHNOLOGY WORLD DMCC, Dubai (AE)

( * ) Notice: Subject to any disclaimer, the term of this patent is extended or adjusted under 35 U.S.C. 154(b) by 0 days.

(21) Appl. No.: 15/540,218

(22) PCT Filed: Dec. 29, 2015

(86) PCT No.: PCT/IB2015/060021
§ 371 (c)(1),
(2) Date: Jun. 27, 2017

(87) PCT Pub. No.: WO2016/108179
PCT Pub. Date: Jul. 7, 2016

(65) Prior Publication Data
US 2017/0358849 A1  Dec. 14, 2017

(30) Foreign Application Priority Data
Dec. 31, 2014  (GB) .................................. 1423380.3

(51) Int. Cl.
*H01Q 1/24* (2006.01)
*H04B 1/3827* (2015.01)
(Continued)

(52) U.S. Cl.
CPC .............. *H01Q 1/245* (2013.01); *A61N 1/16* (2013.01); *A61N 1/323* (2013.01); *A61N 2/02* (2013.01);
(Continued)

(58) Field of Classification Search
CPC .......... H01Q 1/245; H01Q 21/29; H01Q 9/04; H01Q 3/26; H04B 1/3838; A61N 2/02; A61N 1/323; A61N 1/16; A61N 2/06
See application file for complete search history.

(56) References Cited

U.S. PATENT DOCUMENTS

| 5,544,665 A | 8/1996 | Litovitz et al. |
| 5,566,685 A | 10/1996 | Litovitz et al. |

(Continued)

FOREIGN PATENT DOCUMENTS

| EP | 2768150 A1 | 8/2014 |
| GB | 2482421 A | 3/1926 |

(Continued)

OTHER PUBLICATIONS

PCT Search Report and Written Opinion dated Jul. 26, 2016 for Application No. PCT/IB2015/060021.
(Continued)

*Primary Examiner* — Yuwen Pan
*Assistant Examiner* — Fatuma G Sherif
(74) *Attorney, Agent, or Firm* — The Dobrusin Law Firm, P.C.; Daniela M. Thompson-Walters

(57) ABSTRACT

A remedial signal for potentially harmful radiation that is emitted by a portable electronic battery powered communication device is implemented directly within the handset of the portable communication device the portable communication device is operated by a microprocessor and the remedial signal module is controlled by an algorithm in the microprocessor wherein the algorithm obtains information concerning radio frequency communications associated with the portable telecommunications device from the transceivers of the device.

19 Claims, 1 Drawing Sheet

(51) Int. Cl.

| | | |
|---|---|---|
| *A61N 1/16* | (2006.01) | |
| *A61N 1/32* | (2006.01) | |
| *A61N 2/02* | (2006.01) | |
| *A61N 2/06* | (2006.01) | |
| *H01Q 3/26* | (2006.01) | |
| *H01Q 9/04* | (2006.01) | |
| *H01Q 21/29* | (2006.01) | |

(52) U.S. Cl.
CPC .............. *A61N 2/06* (2013.01); *H01Q 3/26* (2013.01); *H01Q 9/04* (2013.01); *H01Q 21/29* (2013.01); *H04B 1/3838* (2013.01)

(56) References Cited

U.S. PATENT DOCUMENTS

| | | | |
|---|---|---|---|
| 6,957,051 B1 | 10/2005 | Korisch et al. | |
| 2011/0090126 A1 | 4/2011 | Szinzi et al. | |
| 2012/0214422 A1* | 8/2012 | Shi ...................... | H04B 1/3838 455/67.11 |
| 2013/0203363 A1* | 8/2013 | Graft ...................... | H04B 1/38 455/73 |
| 2013/0303092 A1* | 11/2013 | Penafiel .............. | H04M 1/0202 455/73 |

FOREIGN PATENT DOCUMENTS

| | | |
|---|---|---|
| GB | 2484167 A | 4/2012 |
| GB | 2484168 A | 4/2012 |
| GB | 2484169 A | 4/2012 |
| WO | 97/19647 A1 | 6/1997 |
| WO | 02/00468 A1 | 1/2002 |
| WO | 2005/112593 A2 | 12/2005 |
| WO | 2012/041514 A1 | 4/2012 |

OTHER PUBLICATIONS

UK Intellectual Property Office Search Report dated Jun. 29, 2015 for Application No. GB1423380.3.
"Cellular Frequencies." *Wikipedia, The Free Encyclopedia.* Last edited on May 31, 2017. Accessed on Jun. 27, 2017. https://en.wikipedia.org/wiki/Cellular_frequencies.
PCT International Preliminary Report on Patentability and Written Opinion dated Jul. 13, 2017 for Application No. PCT/IB2015/060021.
Extended European Search Report for Application No. 15875345.9 dated Jul. 25, 2018.
Second Examination Report for Australian Patent Application No. 2015373164 dated May 28, 2020.

* cited by examiner

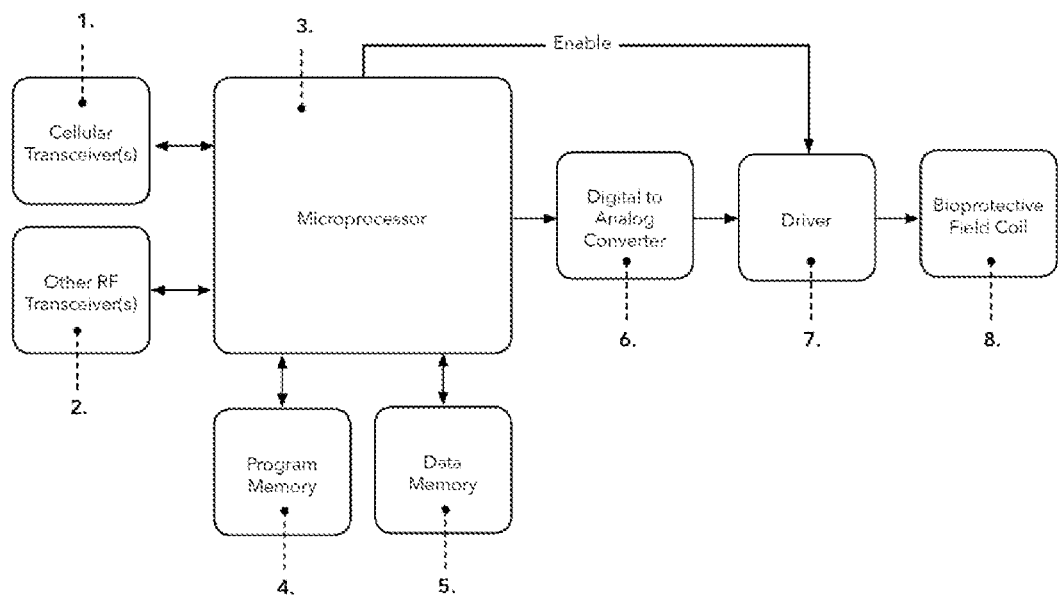

TELEPHONE HANDSET PROVIDED WITH A REMEDIAL SIGNAL GENERATOR

FIELD

The present invention relates to methods and apparatus for protecting living systems from potentially adverse effects upon them from electric fields, magnetic fields and electromagnetic fields. The invention is particularly concerned with protection from potentially adverse radiation from modern day battery powered mobile telecommunications handsets which are used for a variety of functions including both voice and data transmission. In particular the invention is concerned with protection when the handset is used in close proximity to the body, in particular the head, as is often the case during voice transmission.

BACKGROUND

All electromagnetic radiation consists of oscillating electric and magnetic fields and the frequency, which is the number of times per second at which the wave oscillates, determines their properties and the use that can be made of them. Frequencies are measured in hertz or Hz, where 1 Hz is one oscillation per second, 1 kHz a thousand, 1 MHz is a million, and GHz, is a thousand million. Frequencies between 30 KHz and 300 GHz are widely used for telecommunications, including broadcast radio and television, and comprise the radio frequency band.

Cellular mobile services operate at frequencies authorised by governments and typically operate within the frequency ranges 800-3000 MHz and they may operate at different frequencies in different countries or continents. Examples of currently authorised frequencies are the following bands to the terrestrial mobile telecommunications IMT-2000: 806-960 MHz, 1,710-2,025 MHz, 2,110-2,200 MHz and 2,500-2,690 MHz. More information can be found at http://en.wikipedia.org/wiki/cellular_frequencies. These frequencies are within the microwave frequency band which encompasses the range between 300 MHz and 300 GHz. Other applications within this range include radar, telecommunication links, satellite communications, weather observation and medical diathermy. This invention is particularly useful with devices that operate on frequencies used for cellular telephones.

A radio frequency wave used to carry information in radio communications is referred to as a carrier wave. The radio frequency carrier wave of any system is produced by the transmitter as a sine wave, or other regular waveform. A carrier wave conveys no information if its properties do not vary in time. If the carrier wave is to convey any information, for instance, speech, music or digitized data, this information has to be added to it in some way. The process of varying one or more properties of a carrier signal with respect to the information that it is to carry is known as modulation. Properties of the carrier wave that may be varied through modulation include for instance, amplitude, frequency, phase or any combination of these. For example, for AM (amplitude modulation) transmission, the electrical signal from a microphone produced by speech or music is used to vary the amplitude of the carrier wave, so that at any instant the size or amplitude of the RF carrier wave is made proportional to the size of the electrical modulating signal. In FM (frequency modulation), the instantaneous frequency of the carrier deviates from the carrier frequency by an amount dependent on the strength of the modulating signal. Phase modulation (PM) is a form of modulation that represents information as variations in the instantaneous phase of a carrier wave. FM and PM are very commonly used for current day radio communications.

A mobile phone (cell phone) sends and receives information (voice messages, text messages, emails, fax, computer data, downloads information etc.) by radio communication. Radio frequency signals are transmitted from the phone to the nearest base station and incoming signals (carrying the information from the source to which the phone user is listening) are sent from the base station to the phone at a slightly different frequency. Base stations link mobile phones to the rest of the mobile and fixed phone network. Once the signal reaches a base station it can be transmitted to the main telephone network, usually by an optical fibre network.

Each base station provides radio coverage to a geographical area known as a cell. Base stations (BS) are connected to one another by a mobile services switching centre (MSC), which tracks calls and transfers them as the caller moves from one cell to the next. An ideal network may be envisaged as consisting of a mesh of hexagonal cells, each with a base station at its centre. The cells overlap at the edges to ensure the mobile phone users always remain within range of the base station. Without sufficient base stations in the right locations, mobile phones will not work. If a person with a mobile phone starts to move out of one cell into another, the controlling network hands over communications to the adjacent base station.

There are conflicting views as to the effects of electric fields, magnetic fields and electromagnetic fields on living systems. However there is considerable evidence showing that certain fields are able to trigger a range of biological effects in various biological systems and that these effects may be damaging to living systems including humans. There are now also a growing number of studies linking mobile phone use to serious health issues such as childhood leukaemia, brain tumours and fertility. It may also be that the detrimental effects are long term and their full impact has not yet been realised. WO 02/00468 recognises that the reaction may be harmful and provides a system that detects radiation and issues a warning if it is considered harmful. It does not however take any remedial action to rectify the situation.

There has been a dramatic increase around the world in the use of electrically operated devices particularly battery powered hand held mobile telephones. All such devices have associated with them electromagnetic field emissions which, to varying degrees, have the potential to affect human health. Of particular interest are devices that transmit radio frequency (RF) signals and are used in close proximity to the human body particularly the head, for instance hand held cellular phones and other personal communication devices. At issue is the possibility that the safety standards under which these devices are manufactured, which establish RF exposure limits to the users of these devices, may not adequately account for effects below the thermal threshold, that is, at exposure levels well below levels that can produce measurable heating and can be attributed to direct energy transfer. The potential for such low level effects is supported by substantial evidence from epidemiologic studies and laboratory research which suggests that any measures that could reduce and/or minimize the effects of such exposure would be beneficial to the users of these devices. Laboratory research also suggests that the severity of impact from RF exposure at non-thermal levels is dependent on the modulation characteristics of the RF signal, in particular amplitude variations in the low frequency envelope. Signals that display a greater degree of regularity have been shown to have greater biological impact.

Modern mobile devices include a wide range of services which employ complex communication schemes operating in different modes (GSM, 3G, 4G etc.). In the operation of such devices, the modulation characteristics of transmitted RF signals can vary substantially depending on the mode of operation and the type of information that is being transmitted, for instance, voice or data. Accordingly, the extent of biological effects can also vary. It is therefore desirable that a remedial system be capable of assessing the nature of the modulation to determine the potential extent of biological impact. Furthermore, such a remedial system should be compact and adaptable for use in different telephone handsets. Additionally it is desirable that the remedial system operates effectively, is only used when required as determined by the mode of operation of the personal communication device and hence consumes little power from the battery to preserve battery life.

U.S. Pat. No. 5,544,665 is concerned with the protection of living systems from the harmful effects of electromagnetic fields and states that certain fields have an effect on the enzyme ornithine decarboxylase. The patent states that the potentially damaging effect can be reduced or eliminated if the detrimental electromagnetic field is altered either by switching the field on and off or superimposing an electromagnetic noise field upon it. The patent further states that the effect can only be reduced if such alteration causes relevant characteristic properties of the field to change in time at intervals of less than 5 seconds and preferably at intervals from 0.1 to 1 second. The characteristic properties that can be changed are said to be frequency, phase, direction, waveform or amplitude. Similar effects are discussed in Bioelectromagnetics 14 395-403 (1993) and Bioelectromagnetics 18 388-395 (1997).

U.S. Pat. No. 5,544,665 dates from 1991 and describes various applications of the bio-protection scheme including applications to cellular telephones of the type available at that time which were bulky and used only for voice transmission. The EMX Corporation has promoted batteries for such cellular telephones that make use of the technology described in U.S. Pat. No. 5,544,665. When used with a cellular phone, these batteries are said to produce an electromagnetic noise field that is superimposed over the local RF field generated by the operation of the telephone for voice transmission thereby causing the total field to be irregular and thus not likely to cause biological effects. The noise was generated by a coil forming part of the battery pack. Activation of the noise was accomplished by monitoring the flow of electric current from the battery to the phone and using this as an indirect means to determine when the phone was transmitting RF fields that were likely to produce biological effects. This activation technique worked reasonably well with older phones but proved to be unreliable with newer phones that now have many more applications that demand power from the battery but do not produce RF fields. Use of such applications could cause false triggering of the noise and potentially unnecessary and unacceptable reduction in battery life.

GB Patent Application 2482421 A provides a system involving a personal communication device such as a mobile telephone and when the device is in operation the system outputs a low frequency modulated RF confusing field from an RF transmitter located within the personal communication device. There is no differentiation of the type of signal emitted by the device and hence the confusing field is applied when it may not be needed, this is costly and the constant generation of the confusing signal is power consuming.

In WO 2012/041514 we describe technology that addresses these issues and provides a process, an apparatus and systems for the reduction or elimination of the potentially harmful effect on humans or animal life caused by exposure to electromagnetic fields produced by devices that operate by transmitting RF signals. The technology comprises a device provided with separate means to reduce or eliminate the potentially harmful effect of the RF signals and further provided with a module that senses and analyse RF fields and assesses their ability to produce biological effects. This module then activates the means to reduce or eliminate the potentially harmful effect of the measured RF signals on humans or animal life based on the outcome of that assessment. The module may be provided as a separate unit within the communication device.

SUMMARY

It has been proposed that a remedial signal for potentially harmful radiation that is emitted by a portable electronic battery powered communication device can be generated by means of a separate circuit provided within the communication device. The circuit comprising an antenna for detecting the potentially harmful radiation, an analytical module that analyses the detected signal to determine if it is potentially harmful, if so to generate a remedial signal which is preferably a low frequency magnetic field. The module being operated by a separate microcontroller which activates the remedial signal generator which has been described as being a component such as a coil associated with the battery of the communication device.

We have now found that such a bioprotection system may be implemented directly within the handset of the portable communication device such as a cellular telephone handset. We have found that this can be accomplished obviating the need for an antenna and other separate components previously required which saves space within the handset and reduces the number of components required so reducing cost and increasing reliability.

The operation of modern day portable telecommunication systems relies on the handset microprocessor which gathers various wireless communication data from the handset transceivers and implements the appropriate activities within the handset. We have found that by the provision of an additional algorithm (the remedial algorithm) within the handset microprocessor the microprocessor can additionally control the operation of a remedial signal module such as a low frequency magnetic field. The algorithm therefore operates within the handset microprocessor and can be stored in the programme memory.

In operation the remedial algorithm obtains information concerning radio frequency communications associated with the portable telecommunication device from the transceivers of the device. Such information includes the RF communications mode (voice or data, GSM, 3G or 4G etc.), and can also include the power level and timing of the RF signal, this information is then used to determine if a remedial signal is required and if so the nature, strength and duration of the signal that should be generated.

BRIEF DESCRIPTION OF DRAWING

FIG. 1 provides a block diagram showing how the mode of operation of the handset can be monitored and the requirements for a remedial signal can be assessed and an appropriate remedial signal activated by an algorithm within the handset microprocessor.

DETAILED DESCRIPTION

Accordingly the invention provides a battery powered personal communication device operated by a microprocessor wherein the microprocessor contains means for assessment of the risk of the generation of potentially harmful radiofrequency radiation produced by such devices together with means activatable according to the assessment of the risk for the activation of a remedial device for the reduction or elimination of the potentially harmful effect on humans or animal life caused by exposure to such radiation.

The design minimizes the number of components required, saves space and is more economical to produce. Additionally it minimizes power consumption. In the preferred embodiment means are provided to monitor the power drain on the battery and the application conditions are monitored and the maximum power drain is set accordingly. Power drain can be set to be at its lowest when the battery is in storage, somewhat higher when the battery is connected to the phone and battery voltage is above a certain acceptable level, and highest but still as low as possible when RF is being generated and needs to be assessed. In all cases battery voltage is measured and in the last two environments both battery voltage and the RF signal are measured. The power management control may conveniently be implemented by software which is executed within the microprocessor.

Rather than depleting the battery by applying the protection signal until the battery is fully depleted, battery monitoring can ensure that sufficient battery life remains to allow for cellular communication. The monitoring function does not consume significant energy, and therefore it need not be disabled. It is one of the many tasks which execute concurrently on the cell phone. By monitoring battery voltage, and limiting protection signal generation to use above a certain battery voltage, the user has the ability of using the cellular telephone near the end of battery life (emergency communications, for example) without the protection signal depleting the battery.

The microprocessor in the handset monitors the communications mode (GSM, 3G, 4G) and handset mode (voice or data) and output power of wireless transceivers in the cell phone. Using this information, the microprocessor determines when to activate the protection signal. In general, amplitude variation patterns for voice transmission are different than for data transmission and are characteristic of signals that are more likely to cause biological effects. Furthermore, voice transmission often implies proximity of the handset to the head which also increases the likelihood of biological effects. Therefore, identification of the communication mode is important in the determination of potential biological impact. Accordingly, identification of the communication modes can be used to determine the required level of the remedial signal. By way of example the microprocessor can differentiate between GSM voice communication mode, GSM data communication mode, 3G or 4G voice communication mode and 3G or 4G data communication mode. The differentiation is preferably performed by an analytical module within the handset microprocessor that is programmed to detect the different communication modes.

The remedial signal can then be activated according to the communication mode and handset mode as determined by the microprocessor and the strength of the remedial signal can be tailored to the mode of operation and the radiation it will generate. For example, if the remedial signal strength in relation to GSM voice communication is deemed to be 100%, for voice communication for 3G, 50% may be sufficient whereas for 3G data communication 25% may be required. The microprocessor can be programmed to cause the remedial signal generator to provide signals of the appropriate strength according to the analysis of the signals received. The remedial signal is preferably a magnetic field, more preferably an unmodulated low frequency magnetic field.

In our preferred design the handset microprocessor operates the entire system and it also operates a timer to check periodically if the potentially harmful signal is present. In operation the microprocessor recognises the communication mode and handset mode that are operating and determines the level of protection that should be applied. The invention therefore employs a microprocessor programmed to recognise key characteristics of the entire phone system to determine whether biological effects are likely to occur and whether the protective signal is required.

The invention therefore allows the strength of the remedial signal to be tailored according to the nature of the potentially harmful radiation which in turn depends upon the detected mode of operation of the telecommunication handset.

In the preferred embodiment means are provided to monitor the power drain and the application conditions are monitored and as discussed the power drain is set accordingly. As discussed the power management control may conveniently be implemented by software which is executed within a microprocessor and many functions can be implemented within such a microprocessor. In particular it can monitor parameters such as battery voltage: sourced from circuit that connects to the battery. The microprocessor monitors the operational modes of the handset. The microprocessor also activates output parameters such as the Bio-protection noise signal. Additional functions which can be implemented in the software include application state classification and power management, implementation of application state monitoring and control algorithms.

The invention may be applied to most electronic devices that operate by transmitting RF signals which could be potentially harmful to human or animal life, but it is particularly useful with battery powered personal communication devices, such as cellular telephones, that are used in close proximity to the human body particularly to the head. The invention provides a system that can be readily used with a variety of mobile phone designs and their associated batteries and accessories.

Earlier studies have shown that RF radiation can cause potentially harmful effects if it is regular, meaning that it has constant properties, and is continuously applied for periods of over 10 seconds and that the potential harm can be substantially eliminated if the regularity period is reduced to no more than 1 second. The means to eliminate the potential harm used in the present invention may superimpose an electromagnetic noise field on the potentially harmful radiation to produce a combined field that is irregular in time, meaning that it does not have constant properties in time, and therefore no longer has the potential to cause harm. Use of the noise field, which is also referred to as the remedial signal, allows for use of the electronic device without altering the manner in which it operates.

The invention is particularly useful with battery operated personal communication devices. In the preferred embodiment the potentially harmful effect of the RF radiation is inhibited by a means that generates an appropriate remedial signal that is superimposed on the RF signal to provide a combined signal that is irregular and therefore has no bio-effecting consequence. Any suitable means may be used but the means may comprise an inductive coil which is activated to produce the remedial signal field, primarily magnetic in nature, employing power from the battery of the cellular telephone.

The preferred system comprises an electronic circuit that comprises a microprocessor that determines the communications mode and handset mode, determines from this the level of protection to apply and then activates the appropriate protection.

The invention therefore provides more specifically, a remedial device within the handset of a battery powered personal communication device that emits RF transmissions potentially harmful to humans or animal life, the remedial device being activated by a microprocessor which determines the communications mode and handset mode and deduces the presence of said RF transmissions. The remedial device includes a remedial signal generator means, being arranged to establish a remedial electromagnetic field in the vicinity of the handset. In a preferred embodiment power management is implemented to conserve battery power. The determination of communication and handset modes differentiates between signals generated by voice communication and those generated by other forms of communication such as data communication and on this basis activates the appropriate remedial signal deemed to be required for the particular communication and/or handset mode.

The mode sensing by the handset microprocessor enables supply of power from the handset battery to said remedial signal generator (or selected parts thereof). The remedial signal generator may include a remedial signal control module, which provides a control signal to the power source, and a control signal to a remedial signal generator module, for generating the desired form of remedial signal. Control of the remedial signal is responsive to the sensing by the microprocessor, and employs the handset microprocessor to execute one or more algorithms for controlling the remedial signal generator.

The remedial signal generator may include a digital noise generator, which is coupled through digital to analogue conversion means and filter means, for providing an analogue form of the remedial signal, to a coil which provides a means for establishing the remedial field in the neighbourhood of the handset.

The radiation with which this invention is particularly concerned is that emitted by the cellular telephone when it is transmitting or receiving information especially voice information and particularly when it is transmitting voice information as this tends to generate more RF signals and in particular when it is transmitting or receiving speech as that is generally the time when the telephone is in closest proximity to the head, and transmission radiation occurs for a significant length of time so increasing the likelihood of the creation of harmful biological effects.

In operation therefore the cellular telephone will be activated for use and may immediately generate the potentially harmful radiation at the particular predetermined frequency. That the radiation may be harmful will be determined by the microprocessor sensing the communication mode and the handset mode in operation and, if deemed to be required the microprocessor will then activate the remedial signal (noise) generator means that converts the constant potentially harmful radiation to a random benign wave pattern. The microprocessor can also detect when communications end and the potentially harmful radiation is no longer being generated and can then deactivate the remedial signal until the next time that it is required. Negation of the potentially harmful effect of the radiation generated by use of a cellular telephone can be achieved with a remedial signal, preferably an electromagnetic signal, having a frequency preferably in the range 30 Hz to 90 Hz preferably in the range 40 Hz to 60 Hz.

The invention is illustrated by reference to the accompanying FIGURE which is a schematic drawing of the components which may be present within a cellular telephone handset (not shown) for performance of the invention.

The handset contains cellular transceivers (1) and other radio frequency transceivers (2) for performing the various functions required of the cellular telephone. The microprocessor (3) operates the transceivers and also receives digital information from the transceivers indicating the mode of operation of the telephone and the extent of the operation. The microprocessor contains program memory (4) and optionally data memory (5). The program memory of the microprocessor assesses the information received from the transceivers and determines if the mode of operation will cause potentially harmful radiation. If this is deemed to be the case the microprocessor will activate the remedial signal generator by sending a digital signal to a digital/analogue converter (6) and the converted signal activates the driver (7) to provide the desired remedial signal from the bioprotective field coil (8).

The invention claimed is:

1. A communication device which emits a potentially harmful radiation in a form of radio frequency signals, wherein the communication device comprises:
   a) a handset;
   b) one or more transceivers in the handset which transmit and receive the radio frequency signals;
   c) a microprocessor within the handset and in communication with the one or more transceivers, wherein the microprocessor is configured to:
      i) operate the communication device, including the one or more transceivers;
      ii) receive and determine a radio frequency communications mode of the radio frequency signals from the one or more transceivers;
      iii) monitor an output power level of the radio frequency signals of the one or more transceivers;
      iv) operate a timer to determine a timing of the radio frequency signals and periodically check if the potentially harmful radiation is present;
      v) determine when to activate a remedial signal by detecting if the potentially harmful radiation is present based on the radio frequency communications mode, the output power level, and the timing of the radio frequency signals;
      vi) determine a nature and a strength of the remedial signal based on the radio frequency communications mode, the output power level, and the timing of the radio frequency signals;
      vii) instruct a remedial signal generator when to activate the remedial signal and the nature and the strength of the remedial signal;
   e) the remedial signal generator within the handset and in communication with the microprocessor and the one or more transceivers, and upon instruction from the microprocessor configured to generate the remedial signal with the nature and the strength as instructed by the microprocessor, and which is an electromagnetic noise field superimposed on the radio frequency signals having the potentially harmful radiation; and wherein the communication device is a portable, electronic, and battery powered communication device.

2. The communication device according to claim 1, wherein the communication device is a cellular telephone handset.

3. The communication device according to claim 1, wherein the radio frequency communications mode includes voice, data, GSM, 3G, 4G, or a combination thereof.

4. The communication device according to claim 1, wherein the radio frequency communications mode and the output power level are used by the microprocessor to also determine a duration of the remedial signal that should be generated.

5. A communication device comprising:
a) a handset;
b) one or more transceivers in the handset which transmit and receive radio frequency signals;
c) a microprocessor located within the handset and in communication with the one or ore transceivers, wherein the microprocessor is configured to:
  i) operate the communication device, including operating the one or more transceivers;
  ii) a means for an assessment of a risk of generation by the communication device of a potentially harmful radio frequency radiation emitted by the communication device, wherein the means for assessment is part of the microprocessor, wherein the means of assessment receives both a radio frequency communications mode and an output power level of the one or more transceivers from the one or more transceivers, and wherein the means of assessment determines a timing of the radio frequency signals and periodically checks if the potentially harmful radio frequency radiation is present;
  iii) a means for activation according to the assessment of the risk to activate a remedial device for reduction or elimination of the potentially harmful radio frequency radiation, wherein the means for activation is part of the microprocessor, and wherein the means for activation instructs the remedial device when to activate a remedial signal and a nature and a strength of the remedial signal;
d) the remedial device configured to generate the remedial signal and in electrical communication with the microprocessor and the one or more transceivers, and upon instruction from the means for activation is configured to generate the remedial signal with the nature and the strength as instructed by the means for activation; and wherein the communication device is a personal communication device which is battery powered.

6. The communication device according to claim 5, wherein the communication device includes a means to monitor a power drain on a battery of the communication device.

7. The communication device according to claim 5, wherein the microprocessor monitors the radio frequency communications mode of the communication device to determine when to activate the remedial signal.

8. The communication device according to claim 7, wherein identification of the radio frequency communications mode is used to determine a required level of the remedial signal; and
wherein the radio frequency communications mode includes voice, data, GSM, 3G, 4G, or a combination thereof.

9. The communication device according to claim 7, wherein identification of the radio frequency communications mode is performed by an analytical module within the microprocessor in the handset that is programmed to detect different communication modes of the personal communication device.

10. The communication device according to claim 5, wherein the microprocessor operates a timer to check if the potentially harmful radio frequency radiation is present.

11. The communication device according to claim 5, wherein the potentially harmful radio frequency radiation is RF radiation and the effect of the RF radiation emitted by the communication device is inhibited by the remedial device that generates the remedial signal that is superimposed on the RF radiation which is emitted to provide a combined signal that is irregular.

12. The communication device according to claim 11, wherein the remedial device is an inductive coil which is activated to produce a remedial signal field and employs power from a battery of the communication device.

13. The communication device according to claim 5, wherein the communication device is a cellular telephone which when activated for use generates radiation;
wherein the microprocessor determines if the radiation may be harmful by sensing the radio frequency communications mode in operation; and
wherein the microprocessor activates a remedial signal generator to provide a signal that converts the potentially harmful radio frequency radiation to a random benign wave pattern if deemed to be required.

14. The communication device according to claim 5, wherein the microprocessor also detects when communications from the communication device end and the potentially harmful radio frequency radiation is no longer being generated and deactivates a remedial signal.

15. The communication device according to claim 8, wherein the radio frequency communications mode and the output power level are used by the microprocessor to determine a duration of a remedial signal that should be generated.

16. A communication device which is a battery powered personal communication device that emits RF transmissions potentially harmful to human or animal life, wherein the communication device comprises:
a) a handset;
b) one or more transceivers within the handset which transmit and receive radio frequency signals;
c) a remedial signal generator within the handset which generates a remedial signal; and
d) a microprocessor within the handset, wherein the microprocessor is configured to:
  i) operate the communication device, including the one or more transceivers and the remedial signal generator;
  ii) determine a radio frequency communications mode of the communication device from the one or more transceivers;
  iii) determine a power output level of the one or more transceivers;
  iv) operate a timer to determine a timing of the RF transmissions;
  v) deduce a presence of the RF transmissions from the radio frequency communications mode, the power output level, and the timing of the RF transmissions; and
  vi) activate the remedial signal generator based on the presence, the radio frequency communications mode, the output power level, and the timing of the RF transmissions; and wherein the remedial signal generator is in communication with the microprocessor and the one or more transceivers, and wherein upon instruction from the microprocessor is configured to generate the remedial signal with a nature and a strength as instructed by the microprocessor.

17. The communication device according to claim 16, wherein the determination of the radio frequency communication modes of the communication device differentiates between signals generated by voice communication and signals generated by other forms of communication; and wherein the remedial signal which is appropriate and deemed to be required for radio frequency communications mode is activated based on the determination.

18. The communication device according to claim 16, wherein the remedial signal generator includes a digital noise generator which is coupled through a digital to analogue conversion means and a filter means to provide an analogue form of the remedial signal to a coil which establishes a remedial field.

19. The communication device according to claim 16, wherein the radio frequency communications mode and the output power level are used by the microprocessor to determine the nature, the strength, and a duration of the remedial signal that should be generated.

* * * * *